United States Patent [19]

Smestad et al.

[11] Patent Number: 4,582,640

[45] Date of Patent: Apr. 15, 1986

[54] INJECTABLE CROSS-LINKED COLLAGEN IMPLANT MATERIAL

[75] Inventors: Thomas L. Smestad, Palo Alto; John McPherson, Sunnyvale; Donald G. Wallace, Menlo Park, all of Calif.

[73] Assignee: Collagen Corporation, Palo Alto, Calif.

[21] Appl. No.: 663,478

[22] Filed: Oct. 22, 1984

Related U.S. Application Data

[63] Continuation-in-part of Ser. No. 561,058, Dec. 13, 1983, abandoned, which is a continuation-in-part of Ser. No. 375,665, May 6, 1982, abandoned, which is a continuation-in-part of Ser. No. 355,879, Mar. 8, 1982, abandoned.

[51] Int. Cl.$^4$ .................. C08L 89/06; A61L 15/04
[52] U.S. Cl. .................. 260/123.7; 514/773; 514/801; 128/DIG. 8
[58] Field of Search .................. 260/123.7; 424/177, 424/359; 128/DIG. 8; 514/2, 773, 801

[56] References Cited

U.S. PATENT DOCUMENTS

| | | | |
|---|---|---|---|
| 3,949,073 | 4/1976 | Daniels et al. | 424/177 |
| 4,140,537 | 2/1979 | Luck et al. | 260/123.7 |
| 4,233,360 | 11/1980 | Luck et al. | 260/123.7 |
| 4,424,208 | 1/1984 | Wallace et al. | 260/112.5 R |

OTHER PUBLICATIONS

Schechter, I., et al, "Prolonged Retention of Glutaraldehyde-Treated Skin Homografts in Humans", *Brit. Journal of Plas. Surg.*, (1975) 28, 198-202.

*Primary Examiner*—John Kight
*Assistant Examiner*—Nathan M. Nutter
*Attorney, Agent, or Firm*—Ciotti & Murashige

[57] ABSTRACT

Cross-linked atelopeptide collagen that is substantially free of residual cross-linking agent is prepared by: reconstituting atelopeptide collagen from solution by neutralizing the solution at a reduced temperature and a hypotonic ionic strength; cross-linking the reconstituted fibers in an aqueous medium at a concentration of 0.1 to 10 mg/ml with glutaraldehyde under conditions that produce cross-linked collagen that when in suspension in physiological saline at a concentration of 35 mg/ml exhibits a shear viscosity whose log varies linearly with the log of the shear rate and is approximated by the formula $$\log \eta \leq -0.96 \log \gamma + 2.3$$

where $\gamma$ is the shear rate in sec$^{-1}$, log $\gamma$ is in the range of $-6$ to $+2$ and $\eta$ is the viscosity of the suspension in Pascal-sec; optionally quenching the cross-linking reaction with an amino acid; and separating the cross-linked atelopeptide collagen from the reaction mixture. This collagen is dispersed in an isotonic aqueous medium for use in soft tissue dermal augmentation and is injectable and forms implants that have excellent persistence.

31 Claims, No Drawings

INJECTABLE CROSS-LINKED COLLAGEN IMPLANT MATERIAL

CROSS-REFERENCE TO RELATED APPLICATIONS

This application is a continuation-in-part of U.S. patent application Ser. No. 561,058 filed Dec. 13, 1983, now abandoned, which in turn is a continuation-in-part of abandoned U.S. patent application Ser. No. 375,665 filed May 6, 1982 which in turn is a continuation-in-part of abandoned U.S. patent application Ser. No. 355,879 filed Mar. 8, 1982.

DESCRIPTION

1. Technical Field

The invention is in the field of body treating compositions and methods. More particularly it concerns an injectable, cross-linked collagen implant material for augmenting soft tissue in mammals.

2. Background Art

Collagen has been used as a pharmaceutical carrier, as a surgical prosthesis (sutures and wound dressings), and as an implant material. Chvapil, et al, *Intl Rev of Connective Tissue Res* (1973) 6:1. In many instances the collagen was cross-linked with chemical agents, radiation, or other means to improve its mechanical properties, decrease its immunogenicity, and/or increase its resistance to resorption. This prior cross-linked collagen was solid in nature. Implants made from solid cross-linked collagen were implanted surgically (i.e., were emplaced through incision).

Oliver, et al, *Clinical Orthopaedics & Related Research* (1976) 115:291–302, *Br J Exp Path* (1980) 61:544–549, and *Conn Tissue Res* (1981) 9:59–62, describe implants made by treating skin with trypsin followed by cross-linking with an aldehyde. The resulting solid collagen implants were reported to maintain their original mass after prolonged implantation. A main problem with such solid implants is that they must be implanted surgically. Other disadvantages are that they are not as deformable as injectable implants and residual glutaraldehyde may cause the implant to lose its flexibility due to continuing in situ cross-linking.

Schechter, et al, *Br J Plas Surg* (1975) 28:198–202 disclose glutaraldehyde cross-linked skin that was soaked in L-alanine after cross-linking. The article postulates that the exposure of the skin to L-alanine blocked residual reactive groups of the aldehyde, thereby preventing the release of toxic molecules generated by such groups.

U.S. Pat. No. 3,949,073 describes the use of atelopeptide solutions of collagen as an injectable implant material for augmenting soft tissue. According to the patent, the collagen is reconstituted before implantation and forms a fibrous mass of tissue when implanted. The patent suggests adding particles of insoluble collagen microfibrils to control the shrinkage of the fibrous mass formed at the augmentation site. ZYDERM ® collagen implant is a commercial embodiment of the material described in the patent and is composed of reconstituted atelopeptide collagen in saline that contains a small amount of a local anesthetic. While this commercial material is remarkably effective, it may shrink in volume after implantation due primarily to absorption of its fluid component by the body. Thus, if volume constancy, sometimes called "persistency", is essential, an additional injection or injections of supplemental implant material is required.

Commonly owned U.S. Pat. No. 4,424,208 describes an injectable dispersion of cross-linked atelopeptide collagen and reconstituted atelopeptide collagen fibers in an aqueous carrier. The dispersion exhibited improved persistence in an animal model as compared to ZYDERM ® collagen implant.

A principal object of the present invention is to provide a cross-linked collagen implant material that is useful for dermal augmentation and that (1) is uniform i.e., it contains only a single physical form of collagen as compared to the two physical collagen forms contained in the implant material of U.S. Pat. No. 4,424,208, (2) has improved injectability as compared to the dispersions of U.S. Pat. No. 4,424,208, and (3) has improved persistence (reduced solubility, enhanced resistance to proteolytic degradation) and resistance to physical deformation relative to ZYDERM ® collagen implant.

DISCLOSURE OF THE INVENTION

One aspect of the invention is a novel cross-linked atelopeptide collagen for use as an injectable aqueous suspension for augmenting soft tissue that:

(a) is substantially free of residual cross-linking agent; and (b) is composed substantially of fibrous particles which when in suspension in physiological saline at a concentration of 35 mg/ml exhibit a shear viscosity whose log varies linearly with the log of the shear rate and is approximated by the formula $$\log \eta \geq -0.96 \log \gamma + 2.3 \tag{1}$$

where $\gamma$ is the shear rate in sec$^{-1}$, log $\gamma$ is in the range of $-6$ to $+2$ and $\eta$ is the shear viscosity of the suspension in Pascal-sec.

Another aspect of the invention is a collagen implant material for use in augmenting soft tissue comprising an aqueous dispersion of the above described chemically cross-linked atelopeptide collagen.

Yet another aspect of the invention is a process for preparing the above described cross-linked atelopeptide collagen comprising reconstituting atelopeptide collagen from an acidic aqueous solution by neutralizing the solution at a reduced temperature and at a hypotonic ionic strength; cross-linking the reconstituted atelopeptide collagen in an aqueous medium at a concentration of about 0.1 to 10 mg/ml with a cross-linking agent that forms covalent bonds with the collagen under conditions sufficient to produce a fibrous cross-linked collagen that when in suspension in physiological saline at a concentration of 35 mg/ml exhibits a shear viscosity whose log varies linearly with the log of the shear rate and is approximated by the formula $$\log \eta \leq -0.96 \log \gamma + 2.3$$

where $\gamma$ is the shear rate in sec$^{-1}$, log $\gamma$ is in the range of $-6$ to $+2$ and $\eta$ is the shear viscosity of the suspension in Pascal-sec; optionally quenching the cross-linking reaction with a quenching agent that reacts with the cross-linking agent; and separating the cross-linked atelopeptide collagen from the reaction mixture.

Still another aspect of the invention is a method for augmenting soft tissue in a living mammal comprising injecting the above described collagen implant material into the mammal at the augmentation site.

MODES FOR CARRYING OUT THE INVENTION

The cross-linked collagen used in the invention may be derived from collagen collected from any number of mammalian sources. The donor need not be genetically similar to the host into which the material is ultimately implanted. Because of their availability, bovine or porcine corium will usually be employed. The first step in making the cross-linked collagen is to prepare atelopeptide collagen in solution from the corium. The animal skin is softened by soaking it in a mild acid and then scraping it to remove hair, epidermis, and fat. The depilated skin is then soaked again in mild acid and then comminuted by grinding, mincing, milling or like physical treatment. The comminution prepares the skin for solubilization.

The divided tissue may be solubilized under nondenaturing conditions by dispersing it in an aqueous medium and digesting it with a proteolytic enzyme other than a collagenase, preferably an enzyme that is active at acidic pHs. Dilute acid solutions at low temperatures will normally be used to avoid denaturation. Mineral acids such as HCl or carboxylic acids such as acetic, malonic or lactic acids may be used. The pH will normally be in the range of about 1.5 to 5, depending on the enzyme used, and the temperature about 5° C. to 25° C. A preferred procedure is to disperse the comminuted tissue in HCl to a concentration of 1 to 5 g/l at a pH of about 2 at 20° C. After the tissue is dispersed the enzyme is added and the mixture is incubated to permit the enzyme to digest the telopeptide and other solubilizable components of the tissue. Enzymes that attack the telopeptide portion of the collagen while not denaturing the helical portion are used. Examples of such enzymes are pepsin and papain. Pepsin is preferred because it is relatively easily deactivated and removed from the solubilized collagen. The enzyme concentration will usually be in the range of about 0.1% to 10% by weight based on the collagen. The incubation period will typically vary from about two days to two weeks. The progress of the solubilization may be monitored by determining the viscosity of the solution. Once the viscosity reaches a substantially constant level, the solubilization is complete. At this point, the enzyme is deactivated (denatured) and removed.

The enzyme may be deactivated by raising the pH of the solution to at least about 7 by adding an alkaline material such as sodium hydroxide. After the enzyme has been denatured the solution is treated to remove denatured enzyme and the portions of the tissue that were digested during the solubilization. Various dialysis, sedimentation, and filtration techniques may be used to effect such removal. See U.S. Pat. Nos. 3,949,073 col 3, lines 10-22 and 4,140,537 col 5, line 48 to col 6, line 34, which disclosures are incorporated herein by reference. A preferred procedure is to first lower the pH by adding acid and then clarify the solution by diatomaceous earth sedimentation. The sediment is filtered and the filtrate is concentrated. The concentrate is then fractionated by ion exchange chromatography and further concentrated to produce a substantially pure atelopeptide collagen solution that may be used to make the cross-linked collagen.

The next step in making the cross-linked collagen is to reconstitute the atelopeptide collagen from solution. The reconstitution is preferably done by neutralizing the solution at reduced temperatures, preferably about 10° C. to 25° C. The ionic strength of the neutralized solution is preferably hypotonic relative to physiological conditions. Ionic strengths in the range of about 0.03 to about 0.1, preferably about 0.06, will typically be used. The neutralization involves raising the pH of the solution by adding an appropriate base or buffer, such as $Na_2HPO_4$ or NaOH, to a level at which the collagen in solution reaggregates into fibrils. Fiber formation occurs under these conditions at pHs in the range of about 4.9 and about 10.0. The final pH is preferably in the range of about 5 and 8. Within this range pHs below about 7 favor formation of fine, soft fibrils whereas pHs above about 7 favor formation of coarser fibrils. Such texture makes the soft fibril dispersion easier to inject. The duration of the fibril formation step will normally be in the range of about ½ to about 18 hr.

The injectability of the ultimate cross-linked product may be enhanced by forcing the suspension of collagen fibers through a screen of defined pore size after or during the reconstitution step. This procedure, called "screening", provides a preferred starting material for the cross-linking step. Screening breaks up any fibrillar aggregates that may be in the reconstituted fiber suspension and gives a more uniform fiber size distribution. A preferred screening protocol is to repeatedly pass the fiber suspension through a 60 mesh stainless steel screen at about 5° C. and a flow rate of about 7-7.5 l/min about 2-3 hr after the fibers precipitate. The suspension is recirculated through the screen for about 4-5 hr, with about 35 passes through the screen being optimum. After the screening the fiber suspension is incubated in the reconstitution medium for about 6 to 15 hr. The screening procedure is not part of the present invention and is considered to be a separate, independent invention of others that will be the subject of a separate, commonly assigned U.S. patent application.

The resulting reconstituted atelopeptide fibrous collagen gel suspension is then cross-linked with a cross-linking agent that forms covalent bonds between itself and the collagen. Usually the agent will be polyfunctional, and more usually bifunctional. The cross-linking conditions are such as to produce a covalently cross-linked collagen that may be formulated as an injectable fluid and that provides an implant that has improved persistence relative to an implant made from a comparable formulation of non-cross-linked fibrous atelopeptide collagen. When this degree of cross-linking has been reached the cross-linking reaction is optionally quenched by adding a quenching agent. The quenching agent forms a water soluble adduct with the cross-linking agent. The concentration of collagen in the suspension at the time of cross-linking, the concentration of cross-linking agent, and the duration of cross-linking reaction are important process conditions as regards obtaining the kind and degree of cross-linking that provides a product having enhanced injectability. The concentration of collagen in the suspension must be sufficiently low to cause the cross-linking to be substantially intrafibrillar rather than interfibrillar. With intrafibrillar cross-linking the collagen particles can still flow, whereas at high collagen concentrations there is significant interparticle cross-linking and the product becomes solid or too viscous to flow. The collagen concentration at the time of cross-linking will usually be in the range of 0.1 to 10 mg/ml, more usually 1 to 5 mg/ml. Aldehydes are preferred cross-linking agents. Examples of aldehydes that may be used to cross-link the collagen are formaldehyde, acetaldehyde, glyoxal pyruvic aldehyde, and dialdehyde starch. Glutaraldehyde is particularly preferred. Compounds that have functional groups that react with the functional groups of the cross-linking agent (e.g., aldehyde group) to form water soluble adducts may be used to quench the cross-linking reaction. Quenching agents that have free amino groups such as amino acids are preferred. Glycine is particularly preferred. The concentration of glutaraldehyde in the reaction mixture will typically be about 0.001% to about 0.05% by weight. The glutaraldehyde reacts with lysine residues of the collagen fibers thereby reducing the number of free lysines per 1000 amino acid residues in the collagen. At the glutaraldehyde concentrations mentioned above, the number of free lysine residues per 1000 residues remaining after cross-linking will be greater than about 15 per 1000, more usually greater than about 20 per 1000. Lysine content may be measured by reducing the cross-linked collagen with borohydride and hydrolyzing the reduced material under vacuum in 5.7N HCl for 24 hr at 100° C. Amino acid analysis may be performed with available analyzers (e.g., a Durrum Model D-500 analyzer) and the lysine residues quantitated by comparing the lysine/alanine ratio to those observed in noncross-linked controls.

The duration of the cross-linking reaction will usually be in the range of one-half hr to about one week. The reaction will normally be carried out at about 10° C. to about 35° C. The quenching agent is added in at least stoichiometric proportions relative to the cross-linking agent.

A particularly preferred cross-linking protocol is: about 3 mg/ml collagen concentration; about 0.01% by weight glutaraldehyde for about 16 hr at approximately 22° C.

After the cross-linking reaction has been terminated the cross-linked atelopeptide collagen product may be washed with an aqueous buffer solution to remove unreacted aldehyde, aldehyde polymers, and, if quenching was employed, unreacted quenching agent and aldehyde-quenching agent adducts. A sodium phosphate-sodium chloride buffer solution, pH 6.9 to 7.4, is preferred. The particle size of the cross-linked collagen is normally substantially less and, when a screened starting material is used, more uniform than that of the cross-linked collagen of U.S. Pat. No. 4,424,208. The particle size of cross-linked collagen made with unscreened starting material is nominally (largest dimension) less than about 750 microns, usually between about 75 and 750 microns. The washed product may be concentrated, such as by filtration or centrifugation, to a suitable protein concentration range, typically about 20 to 65 mg/ml, more usually about 25 to 40 mg/ml. Protein concentration may be adjusted to this range by addition of buffer or further concentration, as the case may be. The washed product will have a free aldehyde content below about 20 ppm and a viscosity in the range of about 700 to about 3000 cp at 22° C., measured by an oscillating disk viscometer which measures dynamic, not steady flow viscosity. (Nametre Co., model 7.006 PBD). A more definitive way of expressing the rheology of aqueous suspensions of the cross-linked collagen is by shear viscosity as measured with a Contraves Rheomat Model 135 (Contraves AG, Zurich, Switzerland) viscometer fitted with a Couette cell. At a concentration of 35 mg/ml in physiological saline the shear viscosity of the cross-linked collagen of the invention measured in this manner is approximated by formula (1) above.

The shear viscosity of similar suspensions of the cross-linked collagen of U.S. Pat. No. 4,424,208 is 2 to 2.5 times greater than the shear viscosity of the suspensions of the present invention made with unscreened starting materials.

Final formulation of the aqueous suspension of cross-linked, quenched collagen will typically involve adjusting the ionic strength of the suspension to isotonicity (i.e., about 0.15 to about 0.2) and adding a local anesthetic, such as lidocaine, to a concentration of about 0.3% by weight to reduce local pain upon injection. The suspension is then loaded into syringes fitted with a #25 gauge or larger gauge needle for injection. In the case of formulations used for dermal augmentation the term "injectable" means the formulation can be dispensed from syringes having a gauge as low as #25 under normal conditions under normal manual pressure without substantial spiking. The above described steps in the process for preparing the novel injectable cross-linked collagen are preferably carried out in sterile conditions using sterile materials.

The above described collagen implant material may be injected intradermally or subcutaneously to augment soft tissue, to repair or correct congenital anomalies, acquired defects or cosmetic defects. Examples of such conditions are congenital anomalies such as hemifacial microsomia, malar and zygomatic hypoplasia, unilateral mammary hypoplasia, pectus excavatum, pectoralis agenesis (Poland's anomaly) and velopharyngeal incompetence secondary to cleft palate repair or submucous cleft palate (as a retropharyngeal implant); acquired defects (post traumatic, post surgical, post infectious) such as depressed scars, subcutaneous atrophy (e.g., secondary to discoid lupis erythematosis), keratotic lesions, enophthalmos in the unucleated eye (also superior sulcus syndrome), acne pitting of the face, linear scleroderma with subcutaneous atrophy, saddle-nose deformity, Romberg's disease and unilateral vocal cord paralysis; and cosmetic defects such as glabellar frown lines, deep nasolabial creases, circum-oral geographical wrinkles, sunken cheeks and mammary hypoplasia.

The following examples illustrate the cross-linked collagen, implant materials made therefrom, the method by which the materials used, and the merits of implants made of these materials. These examples are not intended to limit the invention in any manner.

PREPARATION OF ATELOPEPTIDE BOVINE COLLAGEN SOLUTION

Bovine hide was softened and depilated by treatment with HCl. The hide was then comminuted and dispersed in HCl, pH 2, at 8-11 g/l. Pepsin was added to the dispersion at 0.1% by weight based on total protein and the mixture was allowed to incubate for about 100-300 hr at 15° C. to 20° C. NaOH was then added to raise the pH of the incubation medium to about 7 and thereby terminate the digestion. The denatured enzyme was removed from the reaction mixture by sedimentation at reduced pH. The solution was then purified and concentrated by filtration and chromatography to form a 3 mg/ml solution of atelopeptide bovine collagen in dilute aqueous HCl, pH 1-4. This solution is hereinafter referred to as CIS.

RECONSTITUTION OF FIBROUS COLLAGEN FROM CIS

Fibrous collagen was reconstituted from CIS by adding 0.02M $Na_2HPO_4$ to the CIS at 15° C. to 22° C. to increase its pH to 7.4±0.2 or 5.8 to 6.5. Fibers were allowed to form for 1–2 hr.

PREPARATION OF CROSS-LINKED VISCOUS COLLAGEN

A. Using Collagen Reconstituted at pH 7.4±0.2.

To one hundred-sixty ml of the neutral reconstituted fibrous collagen suspension was added 1.62 ml of 1.0% aqueous glutaraldehyde at pH 3. The glutaraldehyde solution was added gradually with stirring to attain a final level of 0.01%. After a reaction period of 16 hr the reaction was quenched by adding 3M glycine to 0.2M. The quench time was one hr. The cross-linked collagen was then washed three times with approximately 100 ml of buffer, 0.02M $Na_2HPO_4$, 0.13M NaCl, pH 7.4, with centrifuging at 17000×g for 5 to 7 min between each wash. The dyanamic viscosity of the collagen was measured by an oscillating disc device (Nametre Co., model 7.006 PBD, measurement at a shear rate of about 5000 $sec^{-1}$) and found to be approximately 700 cp at 22° C. After the final wash and centrifugation the collagen was resuspended in the buffer to a protein concentration of about 18.8 mg/ml. This dispersion was loaded into syringes fitted with a #27 gauge needle. This collagen preparation is hereinafter designated preparation C.

Preparations of injectable cross-linked collagen fluid were carried out as above using differing cross-linking reaction times, glutaraldehyde concentrations and final protein concentrations. These preparations are listed below.

| Preparation Designation | % Glutaraldehyde | Reaction Time (hr) | Final Protein Concentration (mg/ml) |
| --- | --- | --- | --- |
| A | 0.01 | 1 | 35 |
| E | 0.05 | 1 | 29.9 |
| G | 0.05 | 16 | 11.4 |

B. Using Collagen Reconstituted at pH 5.8 to 6.5.

One % aqueous glutaraldehyde, pH 3, was added to the reconstituted fibrous collagen dispersion gradually with stirring to give a final glutaraldehyde concentration of 0.005%–0.01%. Cross-linking was allowed to proceed with stirring for 16 hr. The reaction was then quenched by adding 2M glycine with stirring to a final concentration of 0.2 to 0.3M. Quenching continued with stirring for 2–3 hr. The quenched, cross-linked collagen was then centrifuged at 16,000×g for 5 to 10 min, harvested, and resuspended in 10 to 40 vol of 0.02M $Na_2HPO_4$, 0.13M NaCl, pH 7.4. This suspension was centrifuged at 16,000×g for 5 to 20 min and the final viscous cross-linked collagen product was harvested. After the final centrifugation the protein concentration was 45±5 mg/ml.

IN VIVO TESTING OF COLLAGEN PREPARATIONS

Sprague-Dawley female rats 45–50 days old weighing 120±20 g were used as implant recipients.

Groups of three rats were implanted with one of preparations A, C, E and G and with ZYDERM® collagen implant as a control material. Each animal was implanted in two sites: the cross-linked collagen preparation in the right suprascapular region; and the control material in the left suprascapular region. Approximately one cc of material per site was injected into the subcutaneum.

All materials were explanted in the fifteenth day post implantation. Host tissues were carefully dissected from the explants, and the wet weights were recorded. The percent weight recovery (persistence) was then calculated from the weight implanted. Weighed specimens were then embedded, sectioned, and stained for histological examination. Stains used included hematoxylin, eosin, and Gomori trichrome.

RESULTS OF TESTING

Summaries of the histological examinations of preparations A, C, E, and G follow:

Preparation A

This material presented a fairly uniform lacey appearance as compared to implants of more highly cross-linked non-glycine quenched preparations. The latter formulations were generally organized into large densely packed segments with intervening clefts. Clefts also occurred within the preparation A implants but they were smaller and fewer in number. Fibroblast infiltration was excellent throughout the substance of the preparation A implants as well as within the small intervening clefts. New collagen synthesis appeared to be occurring within the clefts. Very few round cells were observed. Vascular channels were good to moderate in the peripheral one-half of the preparation A implants and were not limited to zones of new collagen synthesis. No evidence of encapsulation was observed. Epithelioid cells and multinucleates were absent.

Preparation C

This material was even more lacey and porous than preparation A. It showed excellent diffuse cell infiltration along with areas of new collagen synthesis. These characteristics, along with the general paucity of round cells, make this material the best of the four preparations from a histological viewpoint.

Preparation E

This preparation was generally less lacey than those cross-linked with 0.01% glutaraldehyde. Fibroblasts were diffusely distributed but fewer in numbers and vascularization was generally limited to the peripheral one-third of the implants. Areas of new collagen synthesis were also observed less frequently.

Preparation G

This preparation exhibited the most uniform lacey porous appearance of all the materials cross-linked with 0.05% glutaraldehyde. Although cell migration into this material was good, focal areas of multinucleates and an increase in the number of round cells were also apparent; this had not been observed in preparations cross-linked with 0.01% glutaraldehyde.

The following table reports the results of the persistence (percent wet weight recovery of carefully dissected explanted material relative to wet weight of implant) evaluations of the preparations and the control materials measured at 17 days post implantation.

| Preparation | Persistence |
| --- | --- |
| A | 77% |
| C | 68 ± 5% |
| E | 82 ± 2% |
| G | 64 ± 5% |
| Control (avg) | 30–40% |

PREPARATION OF CROSS-LINKED VISCOUS COLLAGEN WITHOUT QUENCHING

Neutral (pH 7.4±0.2) reconstituted fibrous collagen prepared as above was used. One % aqueous glutaraldehyde was added to two parts by volume of the reconstituted fibrous collagen to a final glutaraldehyde concentration of 0.01%. The mixture was mixed for 10 min and incubated for 16 hr at room temperature. For comparison, one part by volume of the mixture was withdrawn, 3M glycine was added to it to a final concentration of 0.2M, and it was incubated for 2 hr. Both aliquots (glycine-quenched and nonquenched) were then centrifuged at 17,000×g for 5 min. The resulting pellets were each resuspended in 250–300 ml buffer, 0.2M $Na_2HPO_4$, 0.13M NaCl, pH 7.4, for 30 min at room temperature and centrifuged at 17,000×g for 25 min. After centrifugation the protein concentrations were checked and adjusted to 30–40 mg/ml by recentrifuging or addition of buffer. The dispersions were homogenized and loaded into syringes fitted with #27 or #30 gauge needles.

IN VIVO TESTING OF NONQUENCHED AND QUENCHED PREPARATIONS

The nonquenched cross-linked dispersion and the comparison quenched cross-linked collagen dispersion described above were subjected to in vivo testing in rats and guinea pigs by the general procedure described above except that 0.5 cc of material per site was injected. The results of the histological and weight persistence analyses indicated there was no significant difference in the biocompatibility of the nonquenched and quenched materials.

PHYSICO-CHEMICAL TESTING OF NONQUENCHED AND QUENCHED MATERIALS

Qualitative evaluations of the ease of extrudability of the materials were made by extruding the materials after storage for up to four weeks at 37° C. through #30 gauge needles and counting the degree and magnitude of spiking (number of spikes>2×minimum force in newtons). These tests indicated that the extrudability of the quenched material was slightly better than the nonquenched material.

Evaluations of the color change of the two materials after storage at 37° C. indicated that the nonquenched material demonstrated significantly less color change than the quenched material.

Assays for protein concentration, pH, free aldehyde, soluble amine, soluble protein and lysine content showed minimal differences between the two materials except for concentrations of free aldehyde (18% less in quenched material) and soluble amine (substantially higher in quenched material).

The conclusion reached from the in vivo and physico-chemical tests on the quenched and nonquenched materials was that the two materials were substantially equivalent functionally and that the quenching step is, therefore, optional.

RHEOLOGY AND CHARACTERIZATION OF CROSS-LINKED COLLAGEN SUSPENSIONS

Nonquenched suspensions of fibrous cross-linked collagen were prepared by the general procedure described above. The buffered noncross-linked collagen fiber suspension was not screened. The pellet was resuspended in physiological saline at 35 mg/ml.

For comparison cross-linked collagen was prepared as described in U.S. Pat. No. 4,424,208 and suspended at 30 mg/ml in physiological saline and in physiological saline in admixture with fibrous collagen (15%), total protein 30 mg/ml, as described in the patent.

Shear viscosities of these suspensions were determined using a Contraves Rheomat Model 135 viscometer (per manufacturer's instructions) over a log shear rate range of −6 to +2 $sec^{-1}$. The log of shear viscosity varied linearly with the log shear rate over this range. The shear viscosities of the patent suspensions were approximately 2 to 2.5 greater than that of the suspension of the invention material.

Samples of each of the suspensions were compressed between microscope slides and examined at 10–25× in a dissecting microscope. Both suspensions of U.S. Pat. No. 4,424,208 expressed ¼ to ⅓ of their volume as free liquid under mild compressive force and the remaining semi-solid residue included fibrous particles having nominal diameters from 117 to 2000 microns. Much less free liquid expressed from the invention suspension at a comparable compressive force with the compressed particles having a fibrous globular shape, 88 to 710 microns nominal diameter.

Modifications of the above described embodiments of the invention that are obvious to those of skill in the biochemical, medical, and/or surgical arts are intended to be within the scope of the following claims.

We claim:

1. A novel cross-linked atelopeptide collagen for use as an injectable aqueous suspension for augmenting soft tissue that:
   (a) is substantially free of residual cross-linking agent;
   (b) has greater than about 15 free lysine residues per 1000 amino acid residues; and
   (c) is composed substantially of fibrous particles which when in suspension in physiological saline at a concentration of 35 mg/ml exhibit a shear viscosity whose log varies linearly with the log of the shear rate and is approximated by the formula $$\log \eta \leq -0.96 \log \gamma + 2.3$$

where $\gamma$ is the shear rate in $sec^{-1}$, log $\gamma$ is in the range of −6 to +2, and $\eta$ is the viscosity of the suspension in Pascal-sec.

2. The collagen of claim 1 wherein the collagen is bovine corium collagen.

3. The collagen of claim 1 wherein the amount of residual cross-linking agent in the collagen is less than about 20 ppm.

4. The collagen of claim 1 wherein the cross-linking agent is one that forms covalent bonds between itself and the collagen.

5. The collagen of claim 4 wherein the cross-linking agent is an aldehyde.

6. The collagen of claim 4 wherein the cross-linking agent is glutaraldehyde.

7. The collagen of claim 6 wherein the number of free lysine residues per 1000 residues is greater than about 20.

8. The collagen of claim 1 wherein the nominal size of the particles is less than about 750 microns.

9. The collagen of claim 8 wherein said size is in the range of about 75 to 750 microns.

10. The collagen of claim 1 wherein the cross-links are substantially intrafibrillar.

11. A process for preparing cross-linked atelopeptide collagen for use as an injectable aqueous suspension for augmenting soft tissue comprising:
 (a) reconstituting atelopeptide collagen from an acidic aqueous solution by neutralizing the solution at a reduced temperature and at a hypotonic ionic strength;
 (b) cross-linking the reconstituted atelopeptide collagen in an aqueous medium at a concentration of about 0.1 to about 10 mg/ml with a cross-linking agent at a concentration of about 0.001% to 0.05% by weight that forms covalent bonds with the collagen under conditions sufficient to produce a fibrous cross-linked collagen that has greater than about 15 free lysine residues per 1000 amino acid residues and that when in suspension in physiological saline at a concentration of 35 mg/ml exhibits a shear viscosity approximated by the formula $$\log \eta \leq -0.96 \log \gamma + 2.3$$

where $\gamma$ is the shear rate in sec$^{-1}$, log $\gamma$ is in the range of $-6$ to $+2$, and $\eta$ is the viscosity of the suspension in Pascal-sec; and
 (c) separating the cross-linked collagen from the cross-linking reaction mixture.

12. The process of claim 11 wherein said concentration of reconstituted atelopeptide collagen in the cross-linking reaction mixture is about 1 to 5 mg/ml.

13. The process of claim 11 wherein the cross-linking agent is an aldehyde.

14. The process of claim 11 wherein the cross-linked atelopeptide collagen contains less than about 20 ppm free reactive cross-linking agent.

15. The process of claim 11 wherein the temperature of step (a) is about 10° C. to about 25° C., the ionic strength of step (a) is about 0.03 to about 0.1, and the final pH of step (a) is in the range of about 4.9 and about 10.0.

16. The process of claim 15 wherein said final pH is in the range of about 5 and 8.

17. The process of claim 11 wherein the cross-linking agent is glutaraldehyde, and the free lysine content of the cross-linked collagen is greater than about 20 lysine residues per 1000 residues.

18. The process of claim 17 wherein the cross-linking reaction of step (b) is carried out for about one-half hour to about one week.

19. The process of claim 11 wherein the cross-linking reaction is quenched with a quenching agent that reacts with the cross-linking agent.

20. The process of claim 19 wherein the quenching agent is glycine.

21. The process of claim 11 wherein the separation of step (c) includes washing the cross-linked atelopeptide collagen to remove other reaction products and unreacted reactants.

22. The process of claim 11 wherein the cross-links are substantially intrafibrillar.

23. The process of claim 11 wherein: the collagen is bovine corium collagen: the temperature of step (a) is about 10° C. to about 25° C.; the ionic strength of step (a) is about 0.03 to about 0.1; the final pH of step (a) is in the range of about 5 and about 8; the cross-linking agent is glutaraldehyde; the concentration of collagen in the cross-linking reaction mixture is about 1 to 5 mg/ml; the cross-linking reaction is carried out for about one-half hour to about one week; the separation includes washing the cross-linked atelopeptide collagen to remove other reaction products and unreacted reactants; and the cross-linked atelopeptide collagen contains less than about 20 ppm reactive aldehyde and has greater than about 20 free lysine residues per 1000 residues.

24. Cross-linked atelopeptide collagen prepared by the process of claim 11.

25. Cross-linked atelopeptide collagen prepared by the process of claim 23.

26. A collagen implant material for use in augmenting soft tissue in mammals comprising an aqueous suspension of the cross-linked atelopeptide collagen of claim 1.

27. A collagen implant material for use in augmenting soft tissue in mammals comprising an aqueous suspension of the cross-linked atelopeptide collagen of claim 24.

28. A collagen implant material for use in augmenting soft tissue in mammals comprising an aqueous suspension of the cross-linked atelopeptide collagen of claim 25.

29. The collagen implant material of claim 26 wherein the concentration of cross-linked atelopeptide collagen in the suspension is about 20 to about 65 mg/ml.

30. A method for augmenting soft tissue in a living mammal comprising injecting the collagen implant material of claim 26 into the mammal at the augmentation site.

31. A method for augmenting soft tissue in a living mammal comprising injecting the collagen implant material of claim 29 into the mammal at the augmentation site.

* * * * *